US010156522B2

United States Patent
Chan et al.

(10) Patent No.: US 10,156,522 B2
(45) Date of Patent: Dec. 18, 2018

(54) PARALLEL ACQUISITION OF SPECTRAL SIGNALS FROM A 2-D LASER BEAM ARRAY

(71) Applicant: The Regents of the University of California, Oakland, CA (US)

(72) Inventors: James W. Chan, Elk Grove, CA (US); Lingbo Kong, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/303,514

(22) PCT Filed: Apr. 14, 2015

(86) PCT No.: PCT/US2015/025812
§ 371 (c)(1),
(2) Date: Oct. 11, 2016

(87) PCT Pub. No.: WO2015/160844
PCT Pub. Date: Oct. 22, 2015

(65) Prior Publication Data
US 2017/0030835 A1    Feb. 2, 2017

Related U.S. Application Data

(60) Provisional application No. 61/981,194, filed on Apr. 17, 2014.

(51) Int. Cl.
*G01N 21/65* (2006.01)
*G01J 3/06* (2006.01)
*G01J 3/44* (2006.01)

(52) U.S. Cl.
CPC ............. *G01N 21/65* (2013.01); *G01J 3/06* (2013.01); *G01J 3/44* (2013.01); *G01N 2201/068* (2013.01); *G01N 2201/06113* (2013.01)

(58) Field of Classification Search
CPC ............ G01N 21/65; G01N 2201/068; G01N 2201/06113; G01J 3/06; G01J 3/44
See application file for complete search history.

(56) References Cited

U.S. PATENT DOCUMENTS

| 4,259,014 A | * | 3/1981 | Talmi | ........................ G01J 3/18 356/328 |
| 5,939,716 A | * | 8/1999 | Neal | ........................ H05H 3/04 250/251 |

(Continued)

OTHER PUBLICATIONS

Creely, C. et al., "Raman Imaging of Neoplastic Cells in Suspension," (proceeding), Optical Trapping and Optical Micromanipulation III, ec. Kishan Dholakia et al., Proc. of SPIE, Aug. 30, 2016, vol. 6326, 63260U, [Online] [Retrieved on Jul. 2, 2015] Retrieved from the Internet<URL:http:www.rayscience.com/holoeye/ProcSPIE_2006_6326_63260U.pdf>.

(Continued)

*Primary Examiner* — Mohamed K Amara
(74) *Attorney, Agent, or Firm* — Fenwick & West LLP

(57) ABSTRACT

Methods and systems for reconstructing individual spectra acquired from laser interrogation spots in a 2D array illuminating a particle are described. A particle is positioned in a 2D array that includes multiple laser interrogation spots. The laser interrogation spots of the particle are detected in the 2D array using a spectrometer. Multifocal spectral patterns are generated based on the laser interrogation spots, and an individual spectrum for each laser interrogation spot is reconstructed based on the plurality of multifocal spectral patterns.

20 Claims, 9 Drawing Sheets

(56) References Cited

U.S. PATENT DOCUMENTS

| | | | |
|---|---|---|---|
| 6,087,182 A * | 7/2000 | Jeng | G01N 21/05 356/72 |
| 6,797,942 B2 * | 9/2004 | Grier | G01N 30/00 250/251 |
| 7,173,711 B2 * | 2/2007 | Dholakia | G21K 1/006 356/450 |
| 8,431,884 B2 | 4/2013 | Grier | |
| 2002/0108859 A1 * | 8/2002 | Wang | B07C 5/34 204/547 |
| 2002/0132316 A1 * | 9/2002 | Wang | B07C 5/34 435/173.9 |
| 2003/0032204 A1 * | 2/2003 | Walt | G21K 1/006 436/518 |
| 2003/0132373 A1 * | 7/2003 | Curtis | B01F 13/0052 250/251 |
| 2004/0207922 A1 * | 10/2004 | Grier | G02B 26/0808 359/614 |
| 2005/0017161 A1 * | 1/2005 | Grier | G02B 21/32 250/251 |
| 2005/0058352 A1 * | 3/2005 | Deliwala | G01J 3/02 382/232 |
| 2005/0094232 A1 * | 5/2005 | Kibar | G01N 30/00 359/204.1 |
| 2006/0131494 A1 * | 6/2006 | Grier | G03H 1/08 250/251 |
| 2006/0234319 A1 * | 10/2006 | Kakui | G01N 21/6428 435/7.23 |
| 2007/0023622 A1 * | 2/2007 | Grier | G03H 1/0005 250/251 |
| 2007/0057211 A1 * | 3/2007 | Bahlman | G01N 21/6452 250/584 |
| 2008/0094675 A1 * | 4/2008 | Roichman | G03H 1/0005 359/15 |
| 2009/0027747 A1 * | 1/2009 | Lee | G01B 9/021 359/15 |
| 2009/0109516 A1 * | 4/2009 | Wang | G03H 1/02 359/290 |

OTHER PUBLICATIONS

De Luca, A., "Phase-Sensitive Detection in Raman Tweezers: Biological Applications," Doctoral Thesis, Universita Di Napoli Federico II Dec. 17, 2008, [Online] [Retrieved on Jul. 6, 2015] Retrieved from the Internet<URL:http://www.fedoa.unina.it/3494/1/PhDthesis_deluca_annachiara.pdf>.

Newport Oriel Product Line, "Cornerstone 130™ Motorized 1/8m Monochromator Models 74000 and 74004," (user manual), Sep. 27, 2007, 33 pp., [Online] [Retrieved on Jul. 6, 2015] Retrieved from the Internet<URL:http://woodall.ece.ucdavis.edu/pdf/oriel_cornerstone_manual.pdf>.

PCT International Search Report and Written Opinion, PCT Application No. PCT/US15/25812, Jul. 31, 2015, 16 pages.

Princeton Instruments, "Spec-10® System," (product manual), Apr. 14, 2010, 44 pages, [Online] [Retrieved on Jul. 6, 2015] Retrieved from the Internet<URL:http://ftp.princetoninstruments.com/public/Manuals/Princeton%20Instruments/Spec-10%20System%20Manual.pdf>.

Sow, C. et al., "Mutliple-Spot Optical Tweezers Created with Microlens Arrays Fabricated by Proton Beam Writing," Appl. Phys. B 78, Mar. 26, 2004, pp. 705-709, [Online] [Retrieved on Jul. 2, 2015] Retrieved from the Internet<URL:http://www.ciba.nus.edu.sg/publications/phy/pho2004_4.pdf>.

Zhang, P. et al., "Multiple-Trap Laser Tweezers Raman Spectroscopy for Simultaneous Monitoring of the Biological Dynamics of Multiple Individual Cells," Opt. Lett., Oct. 7, 2010, vol. 35, Iss. 20, pp. 3321-3323, [Online] [Retrieved on Jul. 2, 2015] Retrieved from the Internet<URL:http://core.ecu.edu/phys/liy/Homepage/Press%20reports/2010%20OL_Z hang.pdf>.

* cited by examiner

FIG. 5A
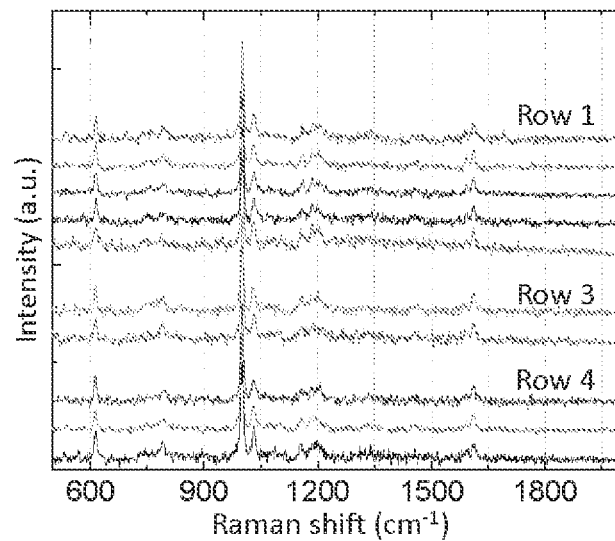
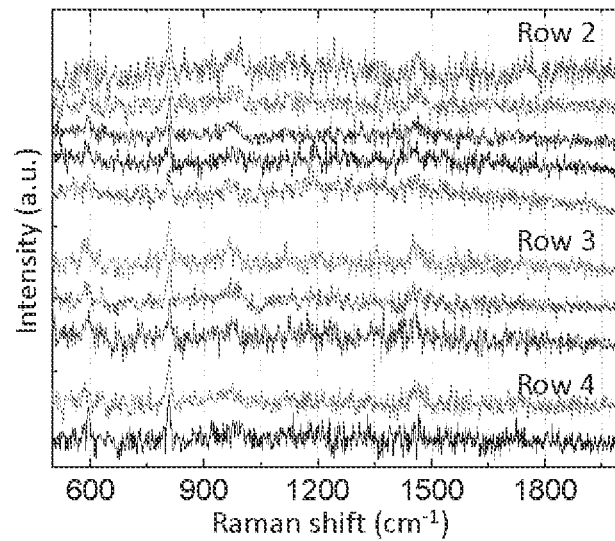
FIG. 5B

10,156,522 B2

PARALLEL ACQUISITION OF SPECTRAL SIGNALS FROM A 2-D LASER BEAM ARRAY

RELATED APPLICATIONS

This application is the National Stage of International Application No. PCT/US2015/025812, filed Apr. 14, 2015, which claims the benefit of U.S. provisional application 61/981,194, filed Apr. 17, 2014, the disclosures of which are hereby incorporated by reference.

STATEMENT REGARDING FEDERALLY SPONSORED RESEARCH OR DEVELOPMENT

This invention was made with government support under grant number 1127888 awarded by the National Science Foundation. The government has certain rights in the invention.

FIELD OF THE INVENTION

The disclosure generally relates to the field of detection of hyperspectral optical signals from multiple sources, or multiple laser spots in a 2-D array, to retrieve the individual spectrum from each laser spot. More specifically, described herein are optical designs and systems for rapid confocal Raman imaging via a multifocal detection scheme for improving the imaging speed of a hyperspectral spontaneous Raman microscope.

BACKGROUND

The ability of the Raman technique to acquire a complete spectrum at each pixel of the sample allows for the generation of Raman maps, or images, that reveal the composition, structure, and distribution of different chemicals in the sample without the use of exogenous labels. As a powerful optical imaging technique, Raman imaging microscopes are in high demand in laboratories and factories for applications including pharmaceutics, forensics, materials and life sciences.

Existing methods of acquiring Raman spectra with a charge-coupled device (CCD) from multiple sources are limited to the sources being aligned in a line. The sources would be arranged so that the signal from each source would be detected by different pixel rows of the CCD. Thus overlap and cross-talk, a problem for Raman spectroscopy due to its generally weak signal strength, would be avoided. In this method however, the number of sources (i.e., samples) for parallel acquisition is limited by the number of pixel rows, usually the vertical dimension, of the CCD. More than one source in a single pixel row would result in a signal with too much cross-talk and the spectra from each source could not be separated. In one example, laser tweezers Raman spectroscopy (LTRS) has been proven useful for analyzing individual cells without need for exogenous labels or extensive sample preparation and perturbation. The utility though would be even greater if cells did not need to be arranged in a single line thereby allowing more cells to be analyzed in a single sample. Additionally, the time-sharing technique that uses only one laser focus makes it difficult to trap a larger number of microparticles (>50).

Furthermore, for current high-resolution confocal Raman imaging products, a single laser focus needs to be scanned point by point in both x- and y-directions to acquire Raman spectra from every pixel, and it will take tens of minutes or hours to form one frame of a Raman image. On the other hand, by using line illumination, line-scan Raman imaging products enable a fast imaging speed with a reduced measurement time of seconds or minutes. However, a line-scan Raman microscope has poor spatial resolution in the line-scan direction compared with the single point scanning confocal Raman microscope. The improvement in imaging speed of the line-scan technique requires a sacrifice in the spatial resolution of the image.

SUMMARY

Disclosed herein are methods for reconstructing individual spectra acquired from a plurality of laser interrogation spots in a two-dimensional (2D) array illuminating a particle. In an embodiment, the method includes positioning a particle in a 2D array, the particle comprising a plurality of laser interrogation spots. The plurality of laser interrogation spots of the particle is then detected in the 2D array using a spectrometer. Next, a plurality of multifocal spectral patterns is generated based on the plurality of laser interrogation spots of the detected particle, and an individual spectrum is reconstructed for each laser interrogation spot based on the plurality of multifocal spectral patterns.

Also disclosed herein are systems for detecting hyperspectral optical signals from a particle and modulating multifocal spectral patterns based on the particle. In an embodiment, the system includes a laser source capable of producing a laser beam for exciting optical signals of the particle. The system also includes a grating-based spectrometer for detecting the hyperspectral optical signals from the activated particle, the spectrometer comprising a slit for achieving high spectral resolution of the hyperspectral optical signals, and for suppressing any background signals that could interfere with the hyperspectral optical signals. The system further includes a multifocal array generator for producing a plurality of multifocal spectral patterns based on the activated particle, and a multifocal array modulator for modulating the plurality of multifocal spectral patterns.

BRIEF DESCRIPTION OF DRAWINGS

FIGS. 5A and B are plots of the individual Raman spectra from FIGS. 3C-F after the calibration procedure, which shows that the Raman peaks for both the polystyrene and the PMMA spectra are well aligned, according to an embodiment.

DETAILED DESCRIPTION

Figure 1:
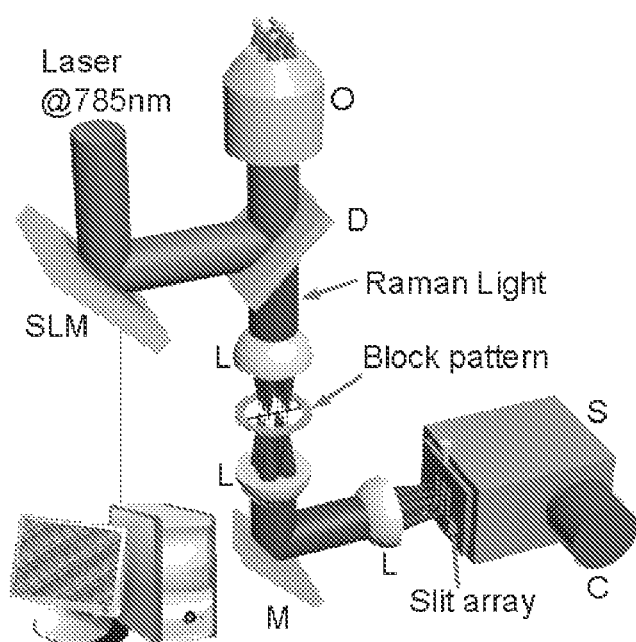
FIG. 1 illustrates one embodiment of an experimental setup used with the disclosed system and method.

The Figures (FIGS.) and the following description relate to preferred embodiments by way of illustration only. It should be noted that from the following discussion, alternative embodiments of the structures and methods disclosed herein will be readily recognized as viable alternatives that may be employed without departing from the principles of what is claimed.

Compared with current Raman imaging techniques, the parallel acquisition system from a 2-D laser focal array as described herein provides capabilities of not only a dramatic improvement in the imaging speed but also maintaining a high spatial resolution. Embodiments of the disclosed systems, methods and computer readable storage mediums include apparatus and methods for acquiring and processing Raman spectral data from multiple sources in a two-dimensional array and outputting an individual spectrum for each source.

Described herein is a method and system for acquiring spectral signals of specimens (or particles) from multiple laser beams (focal spots, for exciting optical signals of the particles) simultaneously, as well as applications for single cell spectroscopy, hyperspectral imaging, and detection of multiple spectra from different spatially independent regions at the same time. The laser beams are produced by a laser source of the system. The methods and systems described herein for particle/specimen spectra can apply to either Raman spectroscopy or other imaging applications. In an embodiment, one or more particles (or specimens) are positioned in a 2D array. A specimen can be a number of particles individually trapped or positioned at each laser focus position, or a large single specimen such that each laser focus is positioned at a different part of the specimen. A spectrometer is then used to detect the laser interrogation spots of the particle or particles.

In some embodiments, a plurality of multifocal spectral patterns at the specimen plane are generated based on laser interrogation spots of one or more particles, using a multifocal array generator such as a microlens array, spatial light modulator (SLM), or scanning galvomirrors. Different multifocal patterns containing superimposed hyperspectral optical signals are created and delivered towards a spectrometer or detector. The spectrometer can be a grating-based spectrometer having a slit for achieving high spectral resolution of the hyperspectral optical signals. The width of the slit determines the optical resolution—the smaller the width of the slit, the higher spectral resolution is achieved. The slit is also used to suppress any background signals that could interfere with the hyperspectral optical signals, since the slit can minimize background signals from entering the spectrometer that would be detected by the camera. A narrower slit allows less background light to enter the detector. Thus, a grating-based spectrometer disperses optical signals so that the different wavelengths can be detected on the camera.

In some embodiments, different 2-D multifocal Raman patterns are generated at a detection arm of the system using different mask patterns, digital micromirror devices, scanning galvomirrors, or spatial light modulators. The multifocal patterns can be delivered as a 2-D array of discrete points at a detection plane that is sent, for example, into a multi-slit spectrometer, or overlapped as a single point into a single array spectrometer (for example, using a descanned galvomirror design). Furthermore, specific multifocal patterns (algorithms) can be used to obtain an optimal signal to noise ratio (SNR) of the reconstructed individual spectra. A camera is generally used to image the spectral signals. For example, the camera can be a 1-D or 2-D pixel array CCD camera, and the camera can operate at low or high acquisition rates (kHz, MHz). In other embodiments, the camera can be a TE cooled back illuminated camera, an EMCCD, an SCMOS, or an InGaAs detector having a linear array of pixels or a 2-D array of pixels. For example, a 1064 nm Raman system can be integrated with InGaAs detectors having a linear array of photodiodes.

In one embodiment, a modulated multifocal detection scheme enables the parallel acquisition of full Raman spectra (~500-2000 $cm^{-1}$) from a 2-D m×n array of optically trapped particles. This design overcomes prior limitations by allowing for parallel detection of spectra along both the vertical and horizontal dimensions of the CCD chip and providing more stable particle trapping. A spatial light modulator (SLM) generates a holographic laser tweezers in a 2-D array. Raman signals from trapped beads are detected simultaneously by a spectrometer equipped with a wide area CCD camera. A shutter system consisting of different mask patterns is placed in the detection path to modulate the 2-D array pattern of Raman signals that was allowed to pass into the spectrometer. In some embodiments, a multifocal array modulator such as an SLM, a slit coupled to the spectrometer, a digital micromirror device, or scanning galvomirror is used to modulate the multifocal spectral patterns. A data processing algorithm is developed to reconstruct the individual Raman spectra of each laser focus based on the different superimposed Raman spectra that were collected from the different multifocal spectral patterns. By allowing the individual Raman spectra from a 2-D multifocal array to be acquired in parallel, this novel system can significantly improve the analytical throughput of LTRS as well as increase the imaging speed of hyperspectral Raman microscopy.

The features and advantages described in the specification are not all inclusive and, in particular, many additional features and advantages will be apparent to one of ordinary skill in the art in view of the drawings, specification, and claims. Moreover, it should be noted that the language used in the specification has been principally selected for readability and instructional purposes, and may not have been selected to delineate or circumscribe the disclosed subject matter.

System FIG. 1 illustrates one embodiment of an experimental setup used with the disclosed systems and methods. A laser beam at 785 nm from a diode laser with a maximum power of 1 W (Sacher Lasertechnik) is illuminated onto a spatial light modulator (SLM) (Boulder Nonlinear Systems). It is noted that the disclosed methods can be used with other wavelengths suitable for Raman spectroscopy subject to standard criteria for selecting a wavelength for Raman interrogation based on various factors, such as a sample type and size. Additionally different power lasers can also be used. The higher the laser power, the more samples can be interrogated at one time.

The SLM is programmed by a computer to modulate the phase of the incident laser beam, which generated a holographic optical tweezers array. The iterative Gerchberg-Saxton (GS) algorithm is used for the hologram calculation (Polin, M.; Ladavac, K.; Lee, S. H.; Roichman, Y.; Grier, D. G.; *Opt. Express* 2005, 13, 5831-5845; Di Leonardo, R.; Ianni, F.; Ruocco, G. *Opt. Express* 2006, 15, 1913-1922). In other embodiments, a microlens array instead of an SLM can be used to generate the laser tweezers array.

Figure 2A:
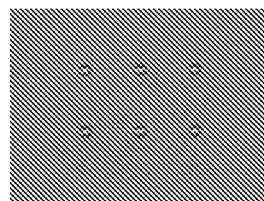
FIG. 2A illustrates a brightfield image of a 2×3 array of polystyrene beads trapped by the laser tweezers array, according to an embodiment.

After passing through a dichroic mirror (D), the phase modulated laser beam from the SLM is directed into an objective (O) (Olympus, 60×/1.2 W) to form the 2-D optical trapping array. FIG. 2A illustrates a brightfield image of a 2×3 array of polystyrene beads trapped by the laser tweezers array. The backward propagating Raman scattering light from the trapped particles was collected by the same objective (O).

Instead of a conventional single slit, a custom designed multi-slit array (HTA Photomask) comprising five mask patterns mounted in a motorized filter wheel (FW102W, Thorlabs) is placed at the entrance of the spectrometer (Princeton Instruments, LS785) in the focal planes of two lenses (L). The general slit array design consists of five 100 μm wide slits spaced 350 μm (center to center) apart to match the dimensions of the array of Raman signals entering the spectrometer. Each mask allows through a different set of four of the five slits. A computer controls the switching of the masks on the filter wheel to be synchronized with the collection of the signal by the CCD. In this embodiment, the program controlling the filter wheel was created in MatLab but other programs can be used as well. In other embodiments, a digital micromirror device (DMD) can be used in place of the filter wheel to modulate the detection pattern. In arrays of larger n, a DMD may be more effective than a filter wheel to modulate rapidly.

Figure 2B:
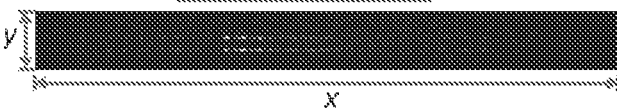
FIG. 2B is a representative image of Raman spectra from a two-dimensional array of trapped particles, according to an embodiment.
Figure 2C:
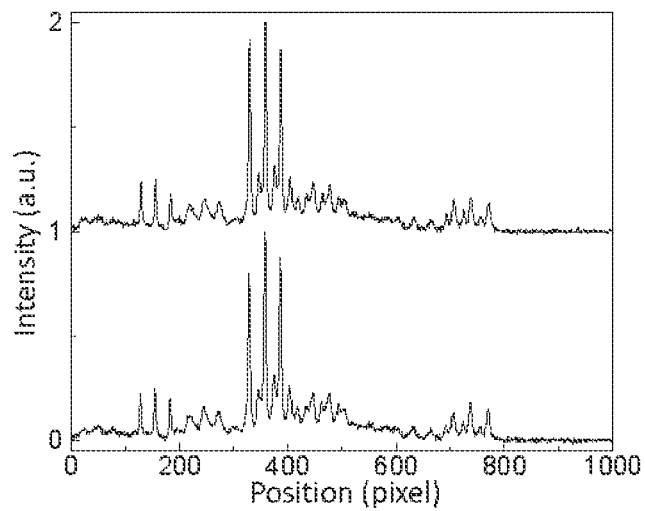
FIG. 2C is a plot of the intensity as a function of pixel position (x direction) for the image in FIG. 2B, according to an embodiment.

The Raman spectral image from all trapped particles is detected by a CCD camera (C) (PIXIS 100BR, Princeton Instruments) mounted onto the spectrometer. FIG. 2B is a representative image of Raman spectra from an array of trapped particles (2×3 in this case) that is captured by the CCD camera. FIG. 2C is a plot of the intensity as a function of pixel position (x direction) for the image in FIG. 2B generated by binning 5 vertical pixels (y direction) for each row in (B).

Figure 6:
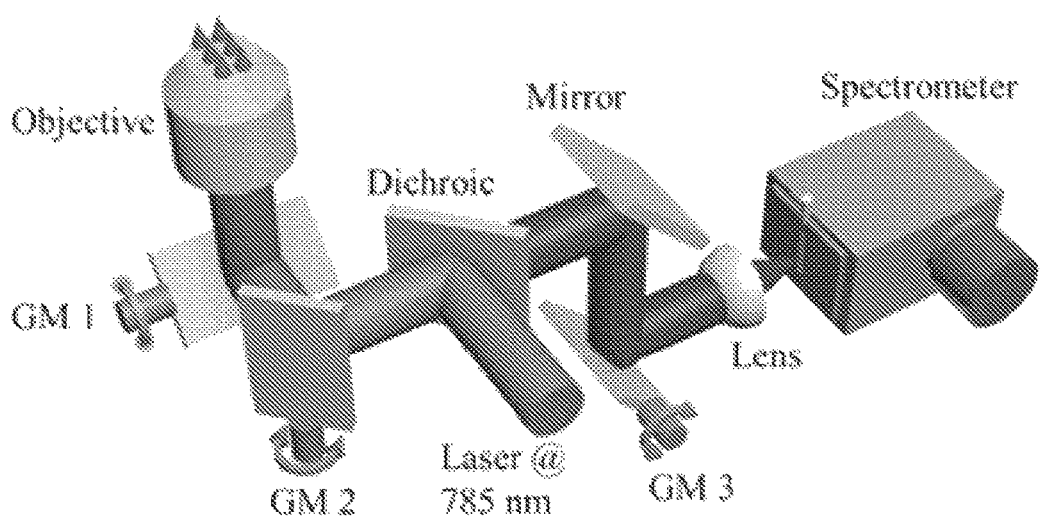
FIG. 6 illustrates a simplified schematic description of parallel detection from a 2D laser foci array for confocal Raman imaging, according to an embodiment.

FIG. 6 illustrates another embodiment of an experimental setup used with the disclosed systems and methods. A pair of galvo-mirrors (GM1 and GM2) replaces the spatial light modulator (SLM) to generate a time-sharing 2-D multifocus array by raster steering the incident Raman excitation laser beam (785 nm). The backward Raman scattering light is separated from the incident laser beam by a dichroic mirror. The third galvo-mirror (GM3) is placed in front of the spectrometer and synchronized with GM1 to project Raman signals from each row of the 2-D laser foci array onto different vertical positions of the CCD chip. In an embodiment, just one slit is used at the entrance of the spectrometer. In another embodiment, a pinhole is placed between the dichroic mirror and the third galvo-mirror to make the best confocal effect for the best spatial resolution of the Raman image.

Figures 7A, 7B:
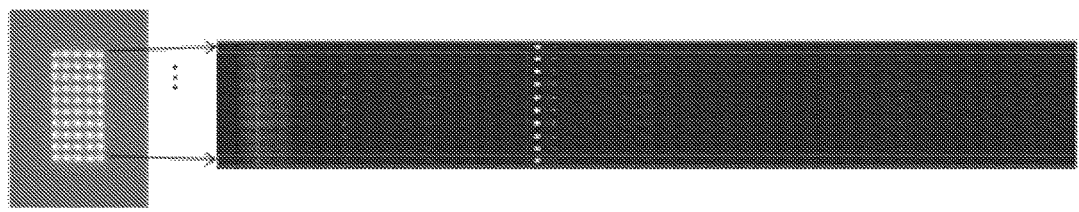
FIG. 7A illustrates an image of 5×10 laser foci array generated by a pair of galvo-mirrors (GM1 and GM2).
FIG. 7B illustrates measurements of 10 Raman signals from the 5×10 laser foci array such that each Raman signal comes from each corresponding row of the laser foci array, according to an embodiment.

FIG. 7A shows an example of 5×10 laser foci array generated by the pair of galvo-mirrors (GM1 and GM2). The 10 rows of Raman signals are detected simultaneously without any cross-talk with the help of a third galvo-mirror (GM3) as shown in FIG. 7B. Each measured Raman spectrum of these 10 signals contains overlapped 5 spectra of each row. In order to resolve the overlapped spectra, 5 modulated laser foci arrays can be easily realized by programming the GM1 and GM2 directly without using any other modulation device. After a total of 5 measurements of these modulated laser foci array patterns, 50 individual Raman spectra from this 5×10 laser foci array can be reconstructed by data processing. For a 10×10 laser foci array, the estimated imaging speed of this system should be ~100 times faster than conventional point-by-point scan system. The imaging system is based on program-controlled three galvo-mirrors which makes the instrument more compact and cost-effective.

Spectral Analysis

Cross-talk between the signals from sources aligned vertically (when a vertical line corresponds to different rows on the CCD) is minimized by adjusting the trap array dimensions and binning the vertical pixels of the CCD chip. In this manner individual Raman spectra for those samples is still obtainable. Spectra for samples aligned horizontally in this configuration overlap each other and thus require additional steps to separate. The below spectral analysis methods can be used with any multifocal array generator described herein. For example, an SLM design can be used with the 4×5 array example described below. If galvomirrors are used, it is possible to overlap beams into a single point instead of using a 2D array. Separating spectra from samples in a two-dimensional is accomplished using matrices. For an array of 20 samples in a 4×5 array, the matrix is:

$$M_0 = \begin{pmatrix} 1 & 1 & 1 & 1 & 1 \\ 1 & 1 & 1 & 1 & 1 \\ 1 & 1 & 1 & 1 & 1 \\ 1 & 1 & 1 & 1 & 1 \end{pmatrix}; \quad (1.1)$$

in which each element of the array represents the Raman spectrum from each individual focus or sample. The samples are measured as many times as there are columns and each time not measuring a different column. In the example of a 4×5 array, this means five different Raman spectral array patterns ($M_i$ (i=1, . . . 5)) are measured to resolve the 20 individual spectra.

$$M_1 = \begin{pmatrix} 0 & 1 & 1 & 1 & 1 \\ 0 & 1 & 1 & 1 & 1 \\ 0 & 1 & 1 & 1 & 1 \\ 0 & 1 & 1 & 1 & 1 \end{pmatrix}, M_2 = \begin{pmatrix} 1 & 0 & 1 & 1 & 1 \\ 1 & 0 & 1 & 1 & 1 \\ 1 & 0 & 1 & 1 & 1 \\ 1 & 0 & 1 & 1 & 1 \end{pmatrix}, \quad (1.2)$$

$$M_3 = \begin{pmatrix} 1 & 1 & 0 & 1 & 1 \\ 1 & 1 & 0 & 1 & 1 \\ 1 & 1 & 0 & 1 & 1 \\ 1 & 1 & 0 & 1 & 1 \end{pmatrix}, M_4 = \begin{pmatrix} 1 & 1 & 1 & 0 & 1 \\ 1 & 1 & 1 & 0 & 1 \\ 1 & 1 & 1 & 0 & 1 \\ 1 & 1 & 1 & 0 & 1 \end{pmatrix},$$

$$M_5 = \begin{pmatrix} 1 & 1 & 1 & 1 & 0 \\ 1 & 1 & 1 & 1 & 0 \\ 1 & 1 & 1 & 1 & 0 \\ 1 & 1 & 1 & 1 & 0 \end{pmatrix};$$

Above 0 in the matrix means no Raman signal is measured for the corresponding trapped particle in the laser trap array. $I_{m,n}$ is defined as the individual Raman spectrum of each trapped particle (m=1, . . . 4; n=1, . . . 5), and $I_{i=1,\ldots,5}^m$ as the overlapped Raman spectra of the m'th row of the i'th designed Raman measurement pattern. The individual Raman spectra of the m'th row can be reconstructed by the following linear equations:

$$\begin{pmatrix} 0 & 1 & 1 & 1 & 1 \\ 1 & 0 & 1 & 1 & 1 \\ 1 & 1 & 0 & 1 & 1 \\ 1 & 1 & 1 & 0 & 1 \\ 1 & 1 & 1 & 1 & 0 \end{pmatrix} \begin{pmatrix} I_{m1} \\ I_{m2} \\ I_{m3} \\ I_{m4} \\ I_{m5} \end{pmatrix} = \begin{pmatrix} I_1^m \\ I_2^m \\ I_3^m \\ I_4^m \\ I_5^m \end{pmatrix}; \quad (1.3)$$

The solutions for these equations are:

$$4(I_{m1}) = I_2^m + I_3^m + I_4^m + I_5^m - 3(I_1^m);$$

$$4(I_{m2}) = I_1^m + I_3^m + I_4^m + I_5^m - 3(I_2^m);$$

$$4(I_{m3}) = I_1^m + I_2^m + I_4^m + I_5^m - 3(I_3^m);$$

$$4(I_{m4}) = I_1^m + I_2^m + I_3^m + I_5^m - 3(I_4^m);$$

$$4(I_{m5}) = I_1^m + I_2^m + I_3^m + I_4^m - 3(I_5^m). \quad (1.4)$$

Processing the data using the above equations yields the 20 individual Raman spectra of each trapped particle in the 2-D array. In some embodiments, Raman spectral array patterns other than the ones described above can yield better individual spectra with improved S/N ratios.

One consideration is the selection and implementation of a modulated multifocal pattern that generates individual reconstructed spectra with optimum signal-to-noise ratio (SNR). For example, consider the following mask patterns that alternatively could have been used:

$$M_1 = \begin{pmatrix} 0 & 1 & 0 & 0 & 1 \\ 0 & 1 & 0 & 0 & 1 \\ 0 & 1 & 0 & 0 & 1 \\ 0 & 1 & 0 & 0 & 1 \end{pmatrix}, M_2 = \begin{pmatrix} 1 & 0 & 1 & 0 & 0 \\ 1 & 0 & 1 & 0 & 0 \\ 1 & 0 & 1 & 0 & 0 \\ 1 & 0 & 1 & 0 & 0 \end{pmatrix}, \quad (1.5)$$

$$M_3 = \begin{pmatrix} 0 & 1 & 0 & 1 & 0 \\ 0 & 1 & 0 & 1 & 0 \\ 0 & 1 & 0 & 1 & 0 \\ 0 & 1 & 0 & 1 & 0 \end{pmatrix}, M_4 = \begin{pmatrix} 0 & 0 & 1 & 0 & 1 \\ 0 & 0 & 1 & 0 & 1 \\ 0 & 0 & 1 & 0 & 1 \\ 0 & 0 & 1 & 0 & 1 \end{pmatrix},$$

$$M_5 = \begin{pmatrix} 1 & 0 & 0 & 1 & 0 \\ 1 & 0 & 0 & 1 & 0 \\ 1 & 0 & 0 & 1 & 0 \\ 1 & 0 & 0 & 1 & 0 \end{pmatrix};$$

The individual Raman spectra of the m'th row can be reconstructed by the following linear equations:

$$\begin{pmatrix} 0 & 1 & 0 & 0 & 1 \\ 1 & 0 & 1 & 0 & 0 \\ 0 & 1 & 0 & 1 & 0 \\ 0 & 0 & 1 & 0 & 1 \\ 1 & 0 & 0 & 1 & 0 \end{pmatrix} \begin{pmatrix} I_{m1} \\ I_{m2} \\ I_{m3} \\ I_{m4} \\ I_{m5} \end{pmatrix} = \begin{pmatrix} I_1^m \\ I_2^m \\ I_3^m \\ I_4^m \\ I_5^m \end{pmatrix}; \quad (1.6)$$

The solutions for these equations are the following (eq. 1.7):

$$2(I_{m1}) = I_1^m + I_2^m - I_3^m - I_4^m + I_5^m;$$

$$2(I_{m2}) = I_1^m + I_2^m + I_3^m - I_4^m - I_5^m;$$

$$2(I_{m3}) = I_1^m + I_2^m + I_3^m + I_4^m + I_5^m;$$

$$2(I_{m4}) = I_1^m - I_2^m + I_3^m + I_4^m + I_5^m;$$

$$2(I_{m5}) = I_1^m - I_2^m - I_3^m + I_4^m + I_5^m;$$

Considering the case as n (the number of foci) becomes larger and larger (i.e. approaches infinity):
If n is an odd number:

$$I_{m1} = \lim_{n \to \infty} \frac{\sum_1^{\frac{n+1}{2}} I_i^m - \sum_1^{\frac{n-1}{2}} I_j^m}{\frac{n-1}{2}}, (i, j = 1, \ldots n; i \neq j)$$

If n is an even number:

$$I_{m1} = \lim_{n \to \infty} \frac{\sum_1^{\frac{n}{2}} I_i^m - \sum_1^{\frac{n}{2}} I_j^m}{\frac{n}{2}}, (i, j = 1, \ldots n; i \neq j)$$

Or in other words: $I_{m1} = I_{qaverage}^m - I_{paverage}^m$

Thus, an individual reconstructed spectrum can be represented as the difference between two averaged spectra of (n−1)/2 or n/2 measurements. Averaged spectra display a reduction in noise as n becomes larger (infinity), and a subtraction operation does not increase the noise level. Hence, the reconstructed individual spectra will have improved SNR compared to a detection scheme without this modulated detection. The key criterion is the selection of patterns that do not produce a multiplying factor in any of the terms in eq. 1.7. In contrast, in equations 1.4, there is a multiplicative factor of 3 in the terms, which increases noise levels.

Example 1

Figures 3A, 3B, 3C, 3D, 3E, 3F:
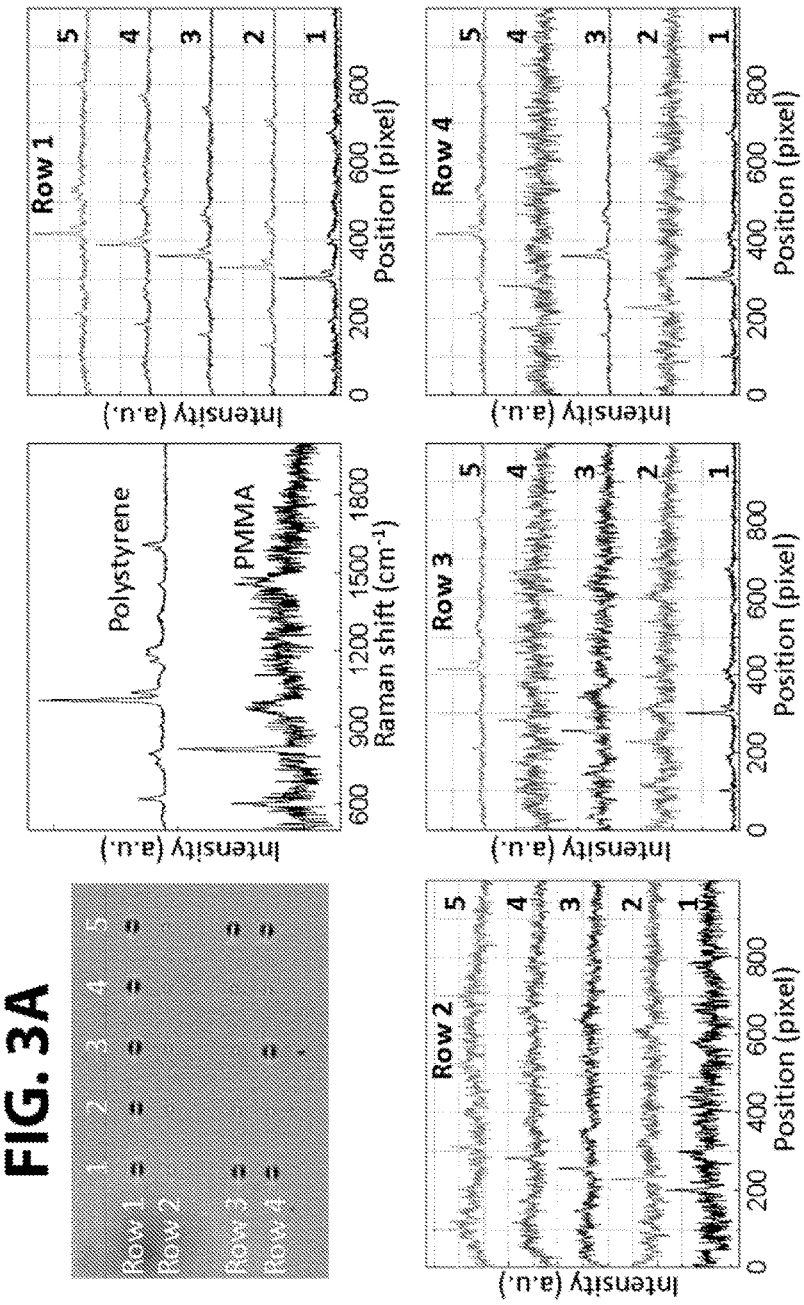
FIG. 3A illustrates a bright field image of a 4×5 array of trapped 3 μm polystyrene and 1 μm poly(methyl methacrylate) (PMMA) beads, according to an embodiment.
FIG. 3B illustrates typical Raman spectra of a single polystyrene and PMMA, according to an embodiment.
FIGS. 3C, 3D, 3E, and 3F illustrate reconstructed spectra of each bead for all four rows, according to an embodiment.

The SLM-based system described above was used to produce spectra of polystyrene and PMMA beads. FIG. 3A shows a bright field image of a 4×5 array of trapped 3 μm polystyrene and 1 μm Poly (methyl methacrylate) (PMMA) beads. Rows 1 and 2 are 3 μm polystyrene beads and 1 μm PMMA beads, respectively, while rows 3 and 4 consist of a random mix of beads. Typical Raman spectra of a single polystyrene and PMMA are shown in FIG. 3B. Using the disclosed system and method, the measured Raman intensity of 3 μm polystyrene bead was ~10 times higher than that of the 1 μm PMMA bead with the same laser power and acquisition times. By switching the filter wheel position to change the measured Raman pattern array as described in the matrices in (1.2), five different Raman signal patterns were collected, each for 2 seconds. Following the data processing using equations (1.4), individual Raman spectra of the 20 trapped beads were reconstructed. FIGS. 3C-F show the reconstructed spectra of each bead for all four rows. Those reconstructed spectra reflect the total time that data was collected from each sample, 8 seconds (4 times 2 seconds).

The signal intensities were plotted as a function of the pixel position on the camera to better visualize the offset of the spectra on the CCD detector in the horizontal dimension. The spectral profile for all beads was accurately reconstructed and matched the standard spectra in FIG. 3B. Because of the index and size differences between the polystyrene and PMMA beads, the beads in each position in the array could be visually identified confirming the accuracy of the reconstructed spectra. Also, the results indicate that there is no spectral crosstalk between the bead samples following the reconstruction algorithm. This is particularly evident in the reconstructed PMMA spectra, which show no spectral contributions from the polystyrene beads, which have a ~10 times stronger signal that would be clearly noticeable if crosstalk was present.

Example 2

Figure 4A:
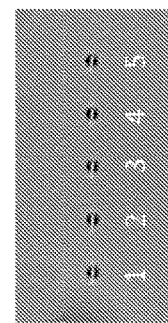
FIGS. 4A and B illustrate a bright-field image of trapped beads in a row, and their corresponding overlapped Raman spectra, which is comprised of the five individual spectra of each bead that pass through the five slits of the slit array, according to an embodiment.
Figure 4B:
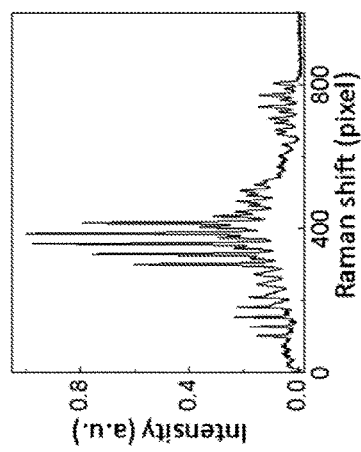
FIG. 4C illustrates the calibrated Raman spectra of polystyrene bead #3, according to an embodiment.
FIG. 4D illustrates a linear relation between each Raman peak position in the CCD chip with the laser trap position, according to an embodiment.
FIG. 4E illustrates that the obtained parameters from a linear fit of the data in FIG. 4E provides for accurate shifting and calibration of the Raman spectra of beads adjacent to bead #3, according to an embodiment.
Figure 4C:
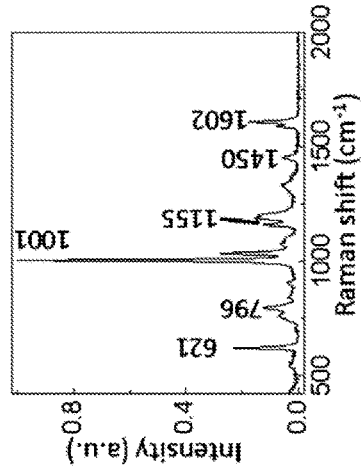
Figure 4D:
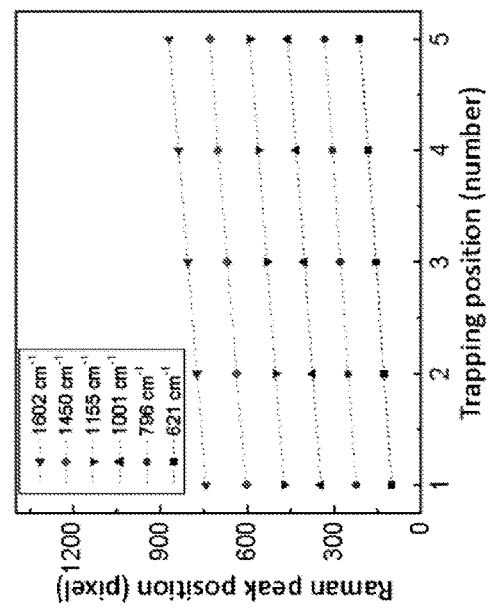
Figure 4E:
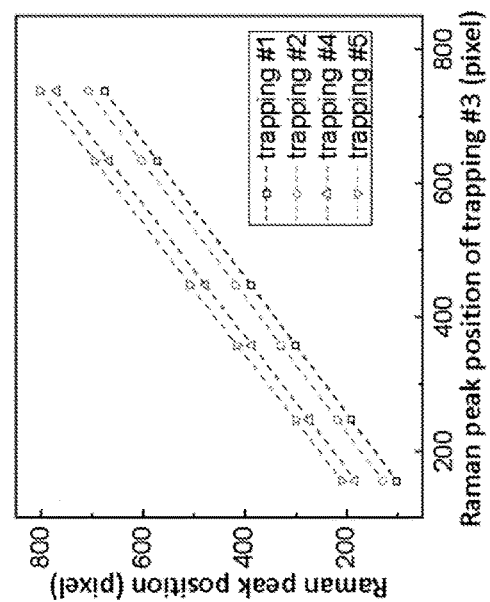

The spectra that are acquired with this multifocal detection scheme of Example 1 are offset along the horizontal axis of the CCD detector. Therefore, the development of a robust and accurate method for calibrating the Raman wavenumbers of these spectra is provided. FIGS. 4A and B illustrate a bright-field image of trapped beads in a row, and their corresponding overlapped Raman spectra, which is comprised of the five individual spectra of each bead that pass through the five slits of the slit array. The central slit that passes the Raman signal of the center bead labeled #3 in FIG. 4A was selected as the standard slit for the wavenumber calibration of the spectrometer. FIG. 4C shows the calibrated Raman spectra of polystyrene bead #3. The Raman spectra of the other four beads are shifted in position along the wave dispersion direction (horizontal x direction) of the spectrometer's CCD chip relative to the spectrum of bead #3. The dependence of the pixel positions of the major polystyrene Raman peaks on the laser trap position (or slit position) of each bead were examined. FIG. 4D shows a linear relation between each Raman peak position in the CCD chip with the laser trap position, which is consistent with previous reported literature (Qi, J.; Li, J. T.; Shih, W. C. *Biomed. Opt. Express* 2013, 4, 2376-2382). However, the slopes of the fitted lines in FIG. 4D are different. For example, the 621, 1001, and 1602 $cm^{-1}$ lines had slopes of 27.2, 28.7, and 31.9, respectively, which indicates that the different Raman peaks are shifted by a different number of pixels. The relative position of the Raman peaks of bead 1, 2, 4, and 5 compared to the peak positions of the center bead #3 were examined. The highly linear relationship that is shown in FIG. 4E indicates that the parameters obtained from a linear fit of the data in FIG. 4E allows for accurate shifting and calibrating the Raman spectra of all the beads adjacent to the center bead #3 and align it to the center position of the spectrometer. FIGS. 5A and B are plots of the individual Raman spectra from FIGS. 3C-F after the calibration procedure, which shows that the Raman peaks for both the polystyrene and the PMMA spectra are well aligned.

Example 3

Figure 8A:
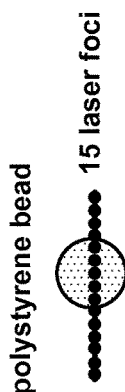
FIG. 8A illustrates 15 laser foci scans across a 3 μm polystyrene bead in a line, according to an embodiment.
Figure 8B:
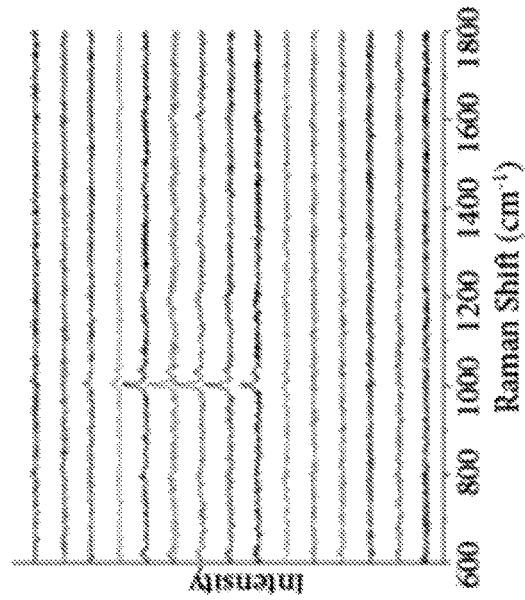
FIG. 8B illustrates Raman spectra by point-by-point scan with a single laser focus, according to an embodiment.
Figure 8C:
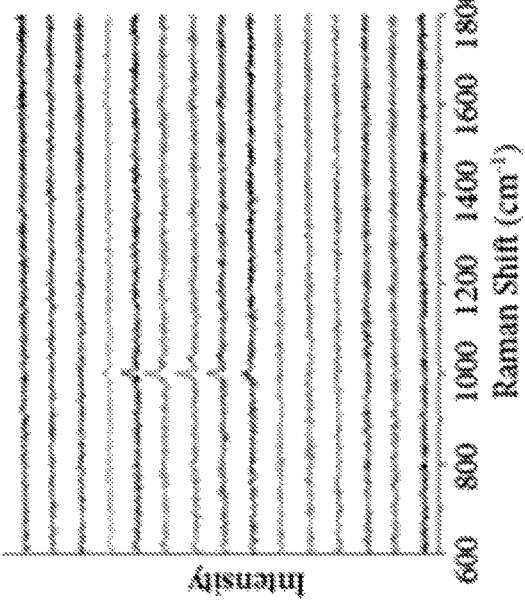
FIG. 8C illustrates reconstructed individual Raman spectra of each point by modulated multifocal detection, according to an embodiment.

The scanning mirror-based system (for example, galvo-mirrors) was used to realize modulated multifocal detection and to produce a better signal-to-noise ratio (SNR) for measured spectra compared with the single point detection. FIG. 8A shows an experiment where 15 laser foci were scanned across a 3 μm polystyrene bead. A NIR spectrometer (LS 785, Princeton Instrument) equipped with a back-illuminated deep depletion CCD (PIXIS 100BR, Princeton Instrument) was used to measure the Raman spectra. The CCD chip was cooled to −80° C. by thermoelectric air-cooling. The read-out noise of the CCD camera is typical 3 $e^{-1}$ rms with read-out rate @ 100 kHz and 11 $e^{-1}$ rms with read-out rate @ 2 MHz. In order to get faster read-out speed, the 2 MHz read-out rate was used in the following measurements. FIG. 8B shows measured 15 spectra of a single laser focus scanning across the polystyrene bead point-by-point with a total 1.5 s acquisition time and 5 mW laser power. For the modulated detection, 15 multifocal patterns as shown in Table 1 were generated by the galvo-mirror GM2 to scan across the polystyrene bead at a mirror scanning rate of 8 KHz. The pattern matrix of 15 line multifocal array in Table 1 is the S-matrix (one type of Hadamard matrices). After 15 detections with these modulated multifocal patterns, 15 individual Raman spectra of each point were reconstructed by the data processing as shown in FIG. 8C. The total acquisition time for modulated multifocal detection is 1 s and the average laser power at each point of multifocal patterns is 5 mW, which are the same experimental conditions as the point-by-point scan with a single laser focus. The calculated SNR of FIG. 8C is improved by more than 2 times compared with FIG. 8B.

TABLE 1

Multifocal Patterns

| No. | Multifocal Pattern (1 or 0 means laser foci are "on" or "off") |
|---|---|
| 1 | 1 0 1 0 1 0 1 0 1 0 1 0 1 0 1 |
| 2 | 0 1 1 0 0 1 1 0 0 1 1 0 0 1 1 |
| 3 | 1 1 0 0 1 1 0 0 1 1 0 0 1 1 0 |
| 4 | 0 0 0 1 1 1 1 0 0 0 0 1 1 1 1 |
| 5 | 1 0 1 1 0 1 0 0 1 0 1 1 0 1 0 |
| 6 | 0 1 1 1 1 0 0 0 0 1 1 1 1 0 0 |
| 7 | 1 1 0 1 0 0 1 0 1 1 0 1 0 0 1 |
| 8 | 0 0 0 0 0 0 0 1 1 1 1 1 1 1 1 |
| 9 | 1 0 1 0 1 0 1 1 0 1 0 1 0 1 0 |
| 10 | 0 1 1 0 0 1 1 1 1 0 0 1 1 0 0 |
| 11 | 1 1 0 0 1 1 0 1 0 0 1 1 0 0 1 |
| 12 | 0 0 0 1 1 1 1 1 1 1 1 0 0 0 0 |
| 13 | 1 0 1 1 0 1 0 1 0 1 0 0 1 0 1 |
| 14 | 0 1 1 1 1 0 0 1 1 0 0 0 0 1 1 |
| 15 | 1 1 0 1 0 0 1 1 0 0 1 0 1 1 0 |

Figure 9:
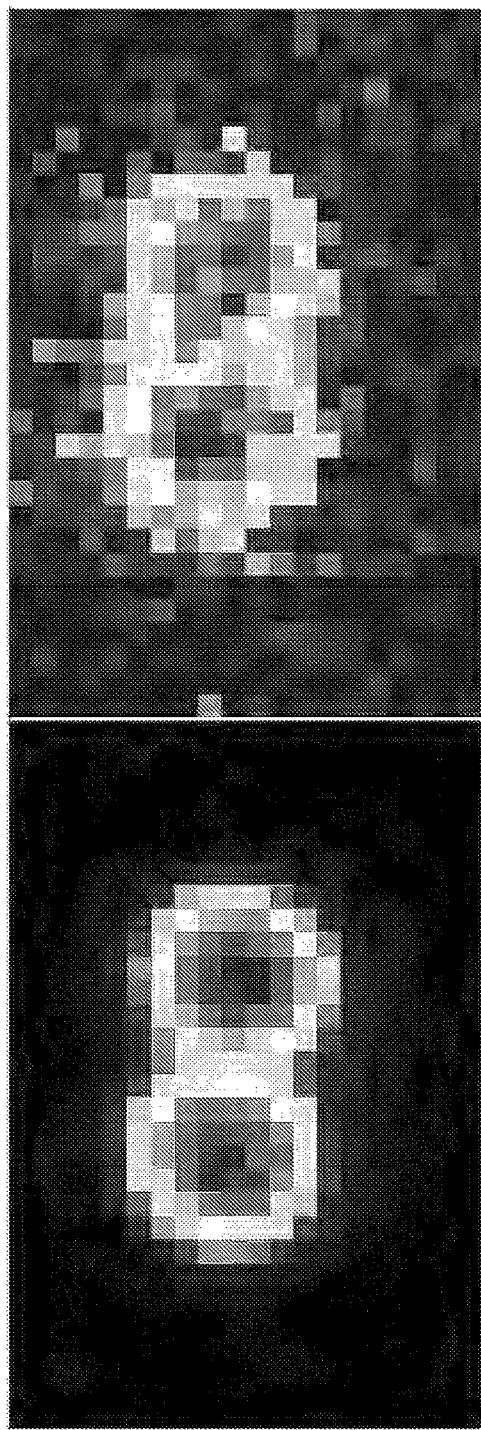
FIG. 9 illustrates a 20×30 pixel Raman image of 3 μm polystyrene beads at 400 nm/pixel, according to an embodiment.

There was a significant improvement of the Raman imaging speed by using the modulated multifocal detection technique when compared with a normal single focus point-scan method. FIG. 9 (left) shows the Raman image of two adjacent 3 μm polystyrene beads (20×30 pixels, 400 nm/pixel, Raman band at 1001 cm$^{-1}$) obtained from a single focus point-scan scheme, in which the laser power is 2 mW at the single focus with 1 s of integration time per pixel. The energy received at each pixel was 2 mJ. The total integration time for the whole Raman image was 600 s. For the modulated multifocal detection scheme, by using the patterns shown in Table 1, 15 patterns were generated by the galvo-mirrors GM1 and GM2. Each pattern was a 10×8 laser foci array formed by the same 10 rows of foci patterns. The third galvo-mirror GM3 was synchronized with GM1 to project 10 rows of corresponding Raman signals onto different vertical positions of the spectrometer's CCD chip. The scan rate was 8 KHz for GM2 and 200 Hz for GM1 and GM3. The integration time for each 10×8 laser foci array pattern was 0.1 s and the energy received at each single pixel point was is set as 2 mJ. After 15 times multifocal pattern measurements, e.g. in a total integration time of 1.5 s, Raman spectra of 150 pixels were obtained simultaneously after data reconstruction processing. Only 6 s of integration time is needed to obtain the 20×30 pixels Raman image as shown in FIG. 9 (right), which has the same dimensions as FIG. 9 (left). Under the same Raman imaging conditions, the imaging speed of this modulated multifocal detection technique was 100 times faster than a single focus point-scan technique.

Additional Considerations

Some of the disclosed embodiments beneficially allow for the reduction of background noise and the confocal detection of the Raman signals. It is contemplated that larger arrays (including, for example 10×10) of samples can be analyzed with the disclosed system and method. The modulation of the detection can also be accomplished by programming different patterns with the SLM. The disclosed multifocal detection scheme can also be used to improve the imaging speed of hyperspectral spontaneous Raman and broadband coherent anti-Stokes Raman scattering (CARS) microscopes. Additionally, the disclosed methods can be applied to hyperspectral parallel detection of optical signals other than Raman.

The disclosed embodiments beneficially allow for reduction of background noise and the confocal detection of the Raman signals.

Various portions of the disclosed system and method can be implemented using a computer. In one embodiment, a computer comprises at least one processor coupled to a chipset. Also coupled to the chipset are a memory, a storage device, a keyboard, a graphics adapter, a pointing device, and a network adapter. A display is coupled to the graphics adapter. In one embodiment, the functionality of the chipset is provided by a memory controller hub and an I/O controller hub. In another embodiment, the memory is coupled directly to the processor instead of the chipset.

The storage device is any device capable of holding data, like a hard drive, compact disk read-only memory (CD-ROM), DVD, or a solid-state memory device. Storage devices include non-transitory tangible computer accessible storage mediums (e.g., RAM, hard disk, or optical/magnetic media), or by equivalent implementations in hardware and/or firmware. The memory holds instructions and data used by the processor. The pointing device may be a mouse, track ball, or other type of pointing device, and is used in combination with the keyboard to input data into the computer system. The graphics adapter displays images and other information on the display. The network adapter couples the computer system to a local or wide area network.

As is known in the art, a computer can have different and/or other components than those described previously. In addition, the computer can lack certain components. Moreover, the storage device can be local and/or remote from the computer (such as embodied within a storage area network (SAN)).

As is known in the art, a computer can be adapted to execute computer program modules for providing functionalities described herein such as the analysis of the collected spectra and also control of various portions of the apparatus including, for example, controlling the multi-slit array. As used herein, the term "module" refers to computer program logic utilized to provide the specified functionality. Thus, a module can be implemented in hardware, firmware, and/or software. In one embodiment, program modules are stored on the storage device, loaded into the memory, and executed by the processor.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

The invention claimed is:

1. A method for reconstructing individual spectra acquired from a plurality of laser interrogation spots in a two-dimensional (2D) array illuminating a particle, comprising:
    positioning the particle in a 2D array, the particle comprising a plurality of laser interrogation spots;
    detecting the plurality of laser interrogation spots of the particle in the 2D array using a spectrometer;
    generating a plurality of multifocal spectral patterns based on the plurality of laser interrogation spots of the particle; and
    reconstructing an individual spectrum for each laser interrogation spot based on the plurality of multifocal spectral patterns; wherein the reconstructing is accomplished using matrices containing columns and rows; wherein each column of the matrix represents each interrogation spot; wherein the particle is measured as many times as there are columns in the matrix; wherein each measurement comprises overlapped spectra of each row of at least one interrogation spot and wherein the individual reconstructed spectrum is represented as an averaged spectra of (n+1)/2 or n/2 measurements of a corresponding interrogation spot; and wherein n is the number of rows.

2. The method of claim 1, wherein the plurality of multifocal spectral patterns and the plurality of laser interrogation spots are generated by a microlens array.

3. The method of claim 1, wherein the plurality of multifocal spectral patterns and the plurality of laser interrogation spots are generated using a spatial light modulator (SLM).

4. The method of claim 3, wherein the plurality of multifocal spectral patterns is further generated using a plurality of mask patterns capable of modulating the plurality of multifocal spectral patterns.

5. The method of claim 3, wherein the SLM generates a holographic laser tweezers in the 2D array for positioning the particle.

6. The method of claim 1, wherein the spectrometer is a multi-slit spectrometer comprising a slit array having a plurality of slits.

7. The method of claim 1, wherein the plurality of multifocal spectral patterns and the plurality of laser interrogation spots are generated using a scanning galvomirror.

8. The method of claim 7, wherein the spectrometer is a single array spectrometer.

9. The method of claim 1, wherein the plurality of multifocal spectral patterns is generated using Raman spectroscopy.

10. The method of claim 1, further comprising imaging the plurality of multifocal spectral patterns using a camera.

11. The method of claim 10, wherein the camera is a TE cooled back illuminated camera, an EMCCD, and SCMOS, or an InGaAs detector having a linear array of pixels or a 2D array of pixels.

12. The method of claim 1, wherein the particle comprises a plurality of particles.

13. A system for detecting hyperspectral optical signals from a particle and modulating multifocal spectral patterns based on the particle, comprising: a laser source capable of producing a laser beam for exciting optical signals of the particle; a grating-based spectrometer, wherein the grating-based spectrometer detects the hyperspectral optical signals from the particle, the spectrometer comprising a slit for achieving high spectral resolution of the hyperspectral optical signals, and for suppressing any background signals that could interfere with the hyperspectral optical signals; a multifocal array generator, wherein the multifocal array generator produces a plurality of multifocal spectral patterns based on the particle; and a multifocal array modulator, configured to modulate the plurality of multifocal spectral patterns; and a computer configured to reconstruct individual spectrum for each laser interrogation spot using matrices containing columns and rows; wherein each column of the matrix represents each interrogation spot; wherein the particle is measured as many times as there are columns in the matrix; wherein each measurement comprises overlapped spectra of each row of at least one interrogation spot; and wherein the individual reconstructed spectrum is represented as an averaged spectra of $(n+1)/2$ or $n/2$ measurements of a corresponding interrogation spot; and wherein n is the number of rows.

14. The system of claim 13, wherein the laser source is a diode laser.

15. The system of claim 13, wherein the multifocal array generator is a microlens array, SLM, or a scanning galvomirror.

16. The system of claim 13, wherein the multifocal array generator comprises a plurality of scanning galvomirrors capable of raster steering the laser beam for generating a multifocal spectral pattern.

17. The system of claim 13, wherein the multifocal array generator comprises an SLM capable of modulating the produced laser beam to trap the particle.

18. The system of claim 13, wherein the multifocal array modulator comprises a plurality of scanning galvomirrors, an SLM, a slit coupled to the spectrometer or a digital micromirror device (DMD).

19. The system of claim 13, wherein the multifocal array modulator is a slit array comprising a plurality of slits, the slit array coupled to the spectrometer.

20. The system of claim 19, wherein the slit array further comprises a plurality of mask patterns mounted in a motorized filter wheel.

* * * * *

UNITED STATES PATENT AND TRADEMARK OFFICE
CERTIFICATE OF CORRECTION

PATENT NO.       : 10,156,522 B2
APPLICATION NO.  : 15/303514
DATED            : December 18, 2018
INVENTOR(S)      : James W. Chan et al.

It is certified that error appears in the above-identified patent and that said Letters Patent is hereby corrected as shown below:

In the Claims

Column 12, Line 60, Claim 1: delete "and" and insert -- ; -- therefor.

Column 14, Line 13, Claim 13: delete "and".

Signed and Sealed this
Twenty-first Day of July, 2020

Andrei Iancu
*Director of the United States Patent and Trademark Office*